United States Patent [19]

Box et al.

[11] Patent Number: 4,832,692
[45] Date of Patent: May 23, 1989

[54] INFLATION SYRINGE ASSEMBLY FOR PERCUTANEOUS TRANSLUMINAL ANGIOPLASTY

[75] Inventors: John W. Box, Miami; John H. Folger, Jr., Lantana, both of Fla.

[73] Assignee: Cordis Corporation, Miami, Fla.

[21] Appl. No.: 918,463

[22] Filed: Oct. 14, 1986

[51] Int. Cl.⁴ ............................................ A61M 29/00
[52] U.S. Cl. ..................................... 604/99; 604/210; 604/211
[58] Field of Search ..................................... 604/97–99, 604/207, 208, 211, 224; 128/344; 401/172, 174, 176; 222/390

[56] References Cited

U.S. PATENT DOCUMENTS

| | | |
|---|---|---|
| 2,221,739 | 11/1940 | Reiter ............................. 604/210 X |
| 2,475,939 | 7/1949 | Applezweig ..................... 604/211 X |
| 4,583,974 | 4/1986 | Kokernak . |
| 4,654,027 | 3/1987 | Dragan et al. . |

*Primary Examiner*—Stephen C. Pellegrino
*Attorney, Agent, or Firm*—Lockwood, Alex, Fitzgibbon & Cummings

[57] ABSTRACT

An inflation device in the form of a syringe assembly for pressurization and depressurization of a ballon catheter includes a manually actuated lever used to disengae a half nut from controlled threaded advancement of a threaded rod which moves a piston. The threaded engagement between the half nut and the rod is such that about one half of the circumference of the rod is engaged, and disengagement movement of the half nut from the rod occurs transversely to the longitudinal axis of the rod.

18 Claims, 2 Drawing Sheets

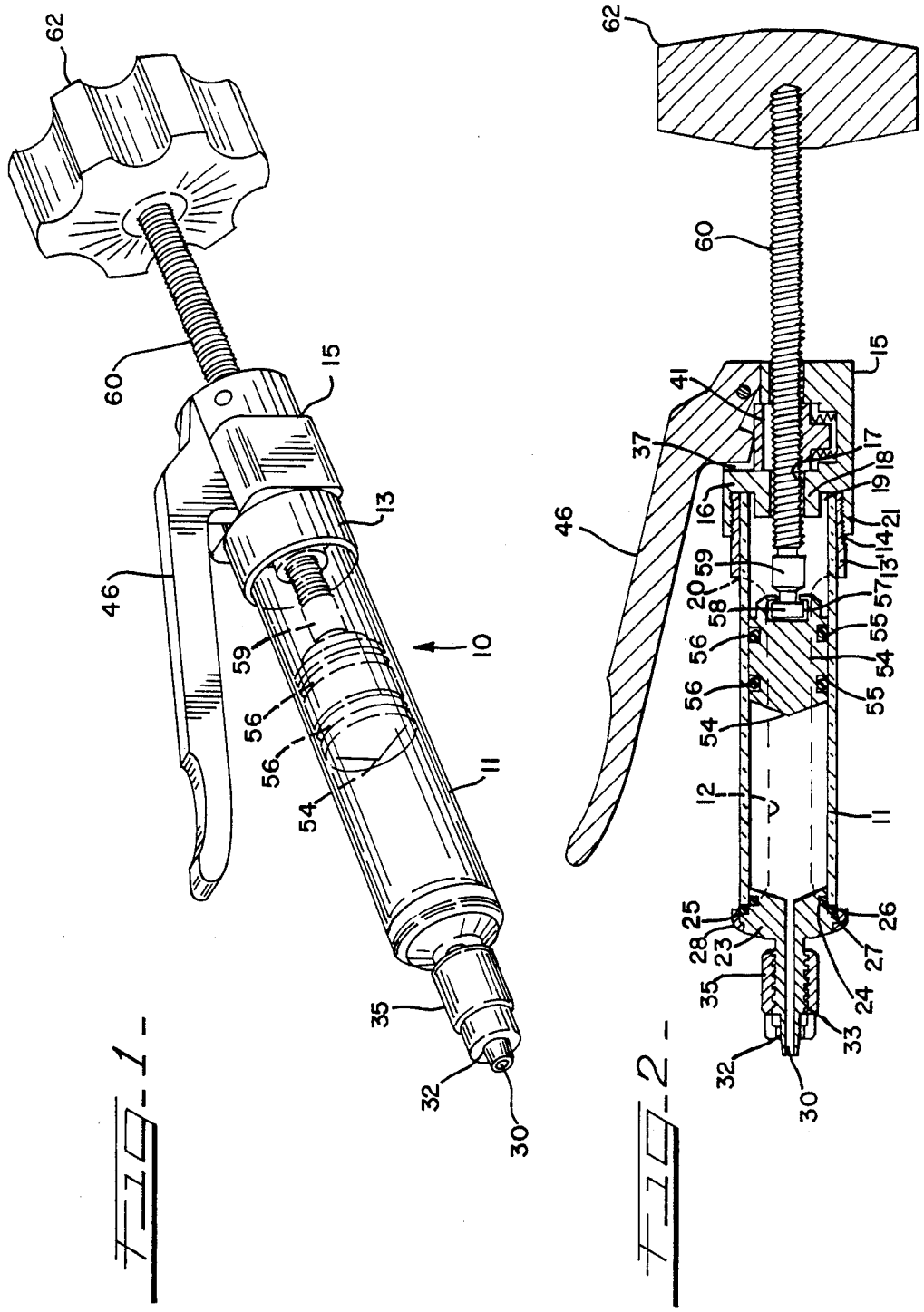

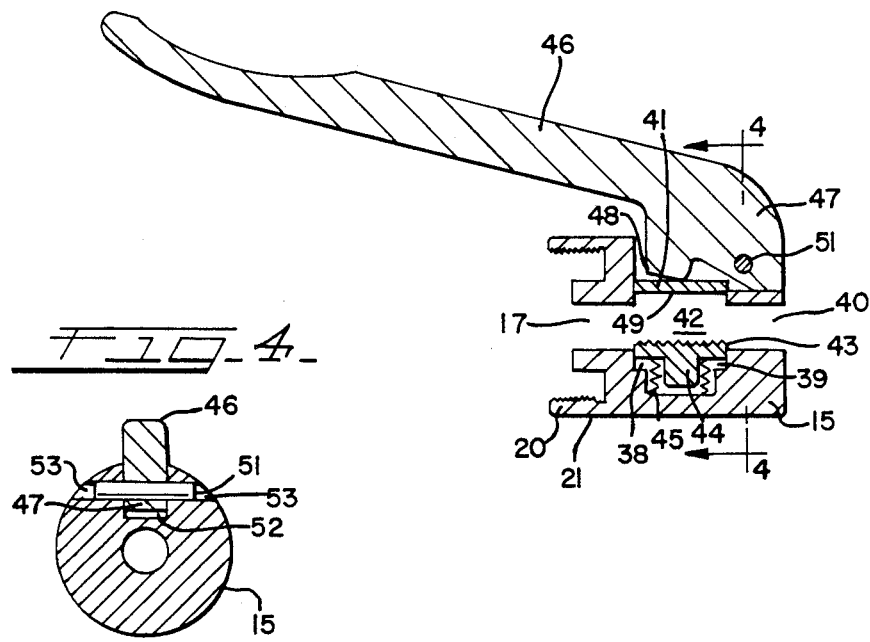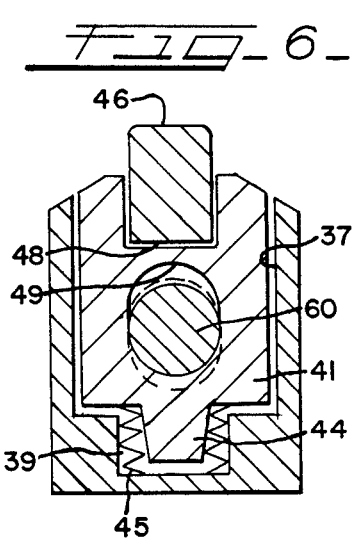

INFLATION SYRINGE ASSEMBLY FOR PERCUTANEOUS TRANSLUMINAL ANGIOPLASTY

BACKGROUND AND DESCRIPTION OF THE INVENTION

The present invention generally relates to components for catheters having inflation devices or balloons for percutaneous transluminal angioplasty, and more particularly to a syringe assembly for inflating and for rapidly deflating an angioplasty balloon component of a catheter to which the inflation syringe assembly is attached.

Great strides have been made in combating blood vessel diseases such as atherosclerosis, which is the increasing deposit of fatty and fibrous plaque that ultimately blocks arteries and other blood vessels. A number of surgical and non-surgical treatments are in use or are proposed. Bypass surgery has been practiced extensively but because of the expense and risks involve,, non-surgical treatments have as of late received particular attention.

Balloon angioplasty, one such non-surgical technique which may be considered to be gaining in popularity, is technically referred to as a percutaneous transluminal angioplasty procedure in which a cardiologist performs the procedure with the patient under local anesthesia. A catheter with a dilatable balloon at or near its tip is threaded into and through an artery and to the stenotic region. The balloon is then inflated thereby compressing the plaque against and into the arterial wall. In this manner the vessel's interior diameter is widened to again permit sufficient flow of blood. This procedure is utilized in the peripheral arteries as well as the coronary arteries.

Typically, the balloon is inflated utilizing a fluid such as a mixture of equal parts of a contrast media and saline solution, which fluid exerts the dilatation pressure. An inflation syringe assembly or device is utilized to deliver the inflation media or fluid to the balloon as well as to provide the pressure needed for dilatation. Continuous pressure readings can be developed by having the inflation syringe assembly coupled in series to a pressure reading device uuch as a manometer.

It is important that the inflation syringe assembly not only deliver fluid and maintain the pressure but also, in particular, release the pressure rapidly when needed. Various designs of syringe assemblies have been utilized and found capable of delivering fluid to a predetermined pressure, but many such devices have been found to be unsatisfactory. Some such devices do not adequately maintain a predetermined pressure for a sufficient period of time as might be required by the physician, such devices tending to "leak" due to inadequate positive pressure control, which adds a further and troublesome complexity to the procedures. In order to obtain the requisite mechanical advantage in positively and incrementally inflating the balloon to higher pressures such as on the order of 450 psi and above, the typical structure provided achieves threaded advancement and usually includes a syringe piston that is advanced by a screw threaded rod engaged with a longitudinally fixed mating threaded member.

This type of positive threaded action usually provides the requisite incremental pressurization of the balloon under controlled conditions, but retraction of the piston at the same slow rate as is needed during advancement is not acceptable in the event that emergency depressurization or the like is necessary. In the event of an emergency or in order to conduct these types of procedures in a manner that avoids unnecessary delays, the balloon must be capable of being deflated as quickly as possible. For purposes of rapid dellation, syringe devices of this type have been constructed with manually movable threadedly mating members which can be disengaged from a threaded rod in an effort to achieve rapid retraction of the threaded rod and its attached syringe piston.

Utilizing the foregoing design approach, certain difficulties have been encountered. For example, it has been found to be extremely difficult to prevent a movable or pivotable threadedly engageable member from being a source of pressure leakage because of a tendency of such member to ride on top of the mating threads of the rod. Thus, proposed designs include the foregoing disadvantage in that the movable or pivotable threadedly engageable member is not sufficiently positively acting and directly responsive through its movement between engaged and disengaged positions. Still further, the rapidity with which the movable threadedly engageable member is completely withdrawn from threaded engagement with the piston rod can be unsatisfactory. While complete disengagement in a time period of on the order of less than one half of a second is extremely important, known devices take at least one second or longer at higher pressures. Furthermore, known devices lack sufficient leverage for rapid disengagement of the threadedly engageable member thus making it extremely difficult, and sometimes impossible, to obtain complete disengagement at pressures of from about 100 to about 150 psi and above.

The inflation syringe assembly of the present invention overcomes these types of shortcomings. By reason of positive engagement between an improved movable partially threaded member and the threaded piston rod, back pressure leakage is eliminated. The movable partially threaded engagement member is structured in such a manner that it rapidly and completely disengages its threaded portion from the piston rod in order to effect almost instantaneous balloon depressurization action by reason of the degree to which it is engageable and disengageable with the rod, as well as due to the direction of its travel to effect engagement and disengagement. Still further, a manually operated lever provides for mechanically advantageous establishment of rapid and positive disengagement that achieves positive and quick disengagement action.

SUMMARY OF THE INVENTION

An inflation syringe assembly for percutaneous transluminal angioplasty is provided with a syringe housing having a movable piston therein coupled with a piston rod that is externally threaded and which projects outwardly of one end of the syringe assembly housing for permitting movement of the piston rod by the physician. A lever housing and assembly having a transversely slidable assembly for selective threaded engagement with the piston rod includes a lever arm that extends externally of the syringe and that is rapidly manually operated with sufficient mechanical advantage to instantly release the threaded engagement between the transversely slidable assembly and the piston rod to permit positive and rapid depressurization of an inflated catheter balloon that is in fluid passing communication with the inflated syringe assembly through a suitable catheter.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of an inflation syringe assembly according to the present invention FIG. 2 is a longitudinal cross-sectional view of an inflation syringe assembly according to the present invention;

FIG. 3 is an enlarged cross-sectional view of the lever assembly forming a part of the inflation device;

FIG. 4 is a cross-sectional view of the lever assembly taken along the line 4—4 of FIG. 3;

FIG. 5 is an enlarged fragmentary cross-sectional view of the lever assembly of the inflation device showing its preferred threaded engagement with the piston rod; and FIG. 6 is a cross-sectional view of the lever assembly and piston rod taken along the line 6—6 of FIG. 5.

DESCRIPTION OF THE PREFERRED EMBODIMENT

The basic design features of the inflation syringe assembly 10 of the present invention are shown in FIGS. 1 and 2. Typical of a syringe, a body 11 is included that is of cylindrical configuration and that is generally transparent. A sleeve 13 covers at least a portion of the body 11. In the embodiment illustrated in FIG. 1, the sleeve 13 covers only the proximal end portion of the body 11, while in FIG. 2, sleeve 13' also includes a protective sheath 20 that extends along the length of the body 11 and that is provided with a plurality of windows or viewing areas 12 (generally illustrated in phantom in FIG. 2) which extend longitudinally and intermediate the ends of the body 11. Typically, measurement markings or graduations are included in order to demarcate relative movement of components and in order to indicate the volume of fluid that is dispersed by the inflation syringe assembly 10.

Proximal portion of the sleeve 13 or 13' has provided along the outer surface thereof a threaded are 14. A support housing 15, which seals the proximal end of the body 11, is provided with an annular cap portion 16 having a centrally located lumen 17 partially defined by an axially projecting inner shoulder 18. Located radially outwardly of shoulder 18 is an annular groove 19 which is radially outwardly defined by an annular shoulder 20 provided with internal threads which mate with the external threads 14 of the collar 13 of th syringe body 11. Groove 19 receives, in a fluid-tight manner, the sleeve 13 or 13' and the body 11, which is preferably formed from a clear generally transparent plastic such as a polycarbonate.

The distal end of the inflation syringe assembly 10 includes a nozzle housing 23 provided with an annular stepped shoulder 24 which seats therein a nozzle gasket 25. Inwardly of shoulder 24 is radially outwardly opening groove 26 which is circumferentially continuous and seats therein a nozzle O-ring 27. The distal end of syringe barrel or body 11 is seated against the gasket 25, and the inner surface of the barrel 11 adjacent the end surface thereof is sealingly engaged by the nozzle O-ring 27. In this manner, syringe barrel 11 establishes a fluid tight seal with the nozzle housing 23. Nozzle housing 23 of the embodiment of FIG. 2 is affixed to the distal end of syringe assembly 10 by means of a radial, inwardly directed annular flange 28 at the distal end of the protective sheath 20. As support housing 15 is threadedly advanced on the proximal end of syringe barrel or body 11 during assembly of the device, the nozzle housing 23 is drawn toward such proximal end resulting in a tight clamping of the syringe barrel 11 between housings 15 and 23 and tight sealing engagement between the distal end of barrel 11 with gasket 25 and O-ring 27.

A central lumen 30 of the nozzle housing 23 extends through the housing 23 and provides fluid communication between the interior of the body or barrel 11 and an outwardly projecting nozzle 32 or the like at the discharge end of the inflation syringe assembly 10. The outer surface of the outwardly projecting portion of nozzle housing 23 is provided with an external threaded portion 33 which mates with an internal threaded portion of a conventional male Linden fitting 35 or the like. This fitting is utilized, for example, to couple the distal nozzle 32 to a pressure manometer (not shown) in the known manner. The distal nozzle 32 thus terminates with a conventional leur taper to facilitate mating with the coupling end of a pressure manometer.

Referring in particular to FIGS. 2, 3 and 6, the support housing 15 that is located outwardly of lumen 17 is provided with chamber 37 that is generally transversely or radially oriented with respect to the longitudinal axis of the inflation syringe assembly 10. Chamber 37 includes an annular shoulder 38 and a recess 39 that extends radially outwardly therefrom. The lumen 17 as well as another lumen 40 open into the chamber 37, and lumens 17 and 40, which are unthreaded and generally smooth, are in axial alignment with each other in order to closely but slidingly receive a piston rod 60 therewithin and through the chamber 37.

Received within chamber 37 of the preferred embodiment is a half nut member 41. The half nut member 41 is provided with an axial lumen 42 which is in communication and general alignment with lumens 17 and 40. Lumen 42 is generally annularly shaped, being somewhat oval in cross-section. A generally semi-circular cylindrical surface of its annular surface that is generally disposed toward the recess 39 is provided with internal threads 43 and an external, radially extending post 44, while an opposing generally semi-circular cylindrical surface 49 is unthreaded and substantially smooth. The threaded surface of the half nut member 41 is biased radially inwardly by a spring-like member or assembly such as the illustrated series of Bellville washers 45 which contact and springingly interconnect the base of recess 39 and the outside surface of the half nut 41. Such spring-like member or assembly preferably generally surrounds the post 44.

As particularly shown in FIGS. 2, 3 and 5, the support housing 15 further includes a lever arm 46 which has a mounting portion 47 having a stop surface 48. The mounting portion 47 includes a transverse aperture receiving a fulcrum pin 51 therethrough. As shown in FIG. 4, the support housing 15 includes a pair of transversely aligned apertures 53 therein, the mounting portion 47 of the lever arm 46 being received within a slot 52 of the support housing 15 and pivotally mounted by means of the fulcrum pin 51. In this manner the lever arm 46 may be pivoted about the fulcrum pin 51 with the stop surface 48 engaging an exposed, radially oriented surface of the half nut 41. When the lever arm 46 is moved generally radially inwardly and pivoted about the fulcrum pin 51, the stop surface 48 pushes on this exposed surface and depresses the half nut 41 into the transverse chamber 37 against the biasing or spring action of the Bellville washers 45 or the like.

The inflation syringe assembly further includes a piston 54 positioned within the lumen 31 of barrel or body 11 and slidable therewithin. Spaced along the outer periphery of the piston 54 is at least one, and preferably a pair of, annular O-ring seats 55 in which O-rings 56 are positioned. In this manner, this piston assembly is sealed against lumen 31 of barrel 11 so as to prevent fluid by-pass during operation of the syringe assembly. The proximal end of piston 54 centrally thereof is provided with a milled slot 57 receiving the enlarged head of a screw attachment member 58. The outer position of the screw attachment member 58 is in the form of a rearwardly opening sleeve 59 which is internally threaded (not shown) and which threadedly receives therein the adjacent end of a piston rod 60. The rod 60 is provided with continuous threads along the outer surface thereof and extends through lumen 17, 40 and 42 of the support housing 15. The proximal end of the piston rod 60 has securely attached thereto a hand knob 62 for grasping by the operator to advance and retract the piston 54 within the syringe barrel 11. The lumens 17 and 40 are of substantially equal diameters and are slightly larger than the outer diameter of the threaded piston rod 60 so that the rod 60 may freely slide through the lumens 17 and 40 during operation of the inflation syringe assembly 10.

Threads 43 of half nut 41 are generally arcuate and preferably engage approximately one half of the circumference of the portion of threaded rod 60 which is received through the generally oval half nut lumen 42. The radially directed urging of the half nut 41 by the Bellville springs 45 or the like establishes this threaded engagement, and while such an engagement exists the operator of the syringe can advance piston 54 only by rotating the hand knob 62 resulting in threaded advancement of rod 60 through half nut 41. During such rotation, the rod 60 can rotate with respect to the piston 54 in order to minimize the effort needed to screwingly advance the piston 54 through the barrel 11. For rapid retraction of the piston 54 within the barrel 11, the hand lever 46 is depressed in the manner previously described resulting in transverse movement of half nut 41 in opposition to the bias or tension provided by the Bellville springs 45 or the like. This results in disengagement of the threads 43 of the half nut 41 from adjacent threads of the piston rod 60 by virtue of generally transverse movement of the half nut 41 along the elongated axis of its generally oval lumen 42 from the thread engaging position shown in FIGS. 2, 3 and 5 to the thread disengaging position shown in phantom in FIG. 6 at which the unthreaded surface 49 permits slidable movement of the rod 60. When this occurs, the piston rod 60 is free to slide through the aligned lumens 17 and 40 as well as through the lumen 42 of the half nut 41 which is thereby rendered operatively unthreaded.

In operation, the percutaneous transluminal angioplasty catheter is advanced through the appropriate blood vessel until the deflated balloon on the distal end of the catheter (not shown) is positioned within the stenotic region. The catheter and the cylinder portion of the inflation syringe assembly 10, which is filled with appropriate fluids such as a mixture of saline solution and contrast media, is typically coupled to a pressure manometer to monitor the pressure developed by the syringe assembly 10. The hand knob 62 of the inflation assembly 10 is rotated thereby advancing the piston and forcing the fluid out of the syringe barrel 11 in order to eventually displace fluid into the balloon to thereby inflate same to the desired size and pressure. To release the pressure in the balloon either normally or in an emergency situation, the lever arm 46 is depressed toward the syringe body forcing the half nut 41 to compress the biasing member 45 thereby releasing the threaded rod 60 from the threads 43 of the half nut 41. Back pressure will force the piston 54 away from the distal or nozzle end until the balloon is deflated. Further deflation and reduction of pressure towards a vacuum or reduced pressure condition can be accomplished by pulling back on the hand knob 62.

While the inflation syringe assembly of the present invention retains the highly desirable mechanical advantage arising from utilization of screw threads for controlled balloon inflation, the pressure release mechanism allows rapid disengagement of the pressurization mechanism. Disengagement of the respective interacting threads of the half nut and of the piston rod is virtually instantaneous, primarily due to the fact that the lever arm acts on the half nut to move the same at a right angle or generally transversely with respect to the longitudinally axis of the threaded piston rod. Threaded disengagement occurs simultaneously, equally and uniformly throughout the axial length of threads 43 of half nut 41. There is virtually no possibility of any of the threads of the half nut riding on top of the threads of the piston rod 60 after the lever arm is depressed as long as the syringe of the subject invention is properly operated.

Thus, if the physician encounters difficulty in balloon inflation, he or she can immediately depress lever arm 46 to obtain split second response resulting in rapid reduction in fluid pressure and immediate balloon deflation. This is of extreme importance particularly in connection with the utilization of higher pressures such as on the order of 450 psi. As pressures build up beyond 100 to 150 psi there is a greater demand for exacting positive disengagement of cooperating threads controlling the advancement and retraction of the piston rod. By reason of the right angle displacement of the half nut relative to the piston rod, the requisite disengagement will occur in less than one-half second. The lever arm 46 and particularly the handle portion thereof is of sufficient length to provide the necessary mechanical advantage t force disengagement between the threads even at the higher pressures. Because of this arrangement and the mechanical advantages attendant thereto, inability to disengage the threads as well as retention of partial overriding engagement between the threads are eliminated.

As best shown in FIG. 6, and as previously described, the arcuate threads 43 of half nut 41 are of sufficient extent within the half nut to engage about one half of the circumference of the piston rod 60. This particular arrangement provides the requisite mechanical advantage needed to establish high pressures in the balloon as well as incremental control of pressure build-up through turning advancement of piston rod 60. While this design feature provides the highly desirable and necessary mechanical advantage described, it does not interfere with the sometimes conflicting requirement of immediate disengagement in the event of an emergency. Thus, the two advantages described are mutually compatible.

The various components of the inflation syringe assembly of the subject invention should be made from material which may be readily sterilized and which remains usable following numerous sterilizations. For example, the basic components may be formed of chrome plated brass while the various gaskets and O-rings may be formed from a suitable fluoroelastomer. The support housing 15, nozzle housing 23, half nut 41, piston 54 and piston rod 60 as well as other internally associated parts may be formed from stainless steel. The inflation syringe described is readily disassembled for complete cleaning and sterilization of all of its parts.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. An inflation syringe assembly for percutaneous transluminal angioplasty, said assembly comprising:
    a housing adapted to receive fluid therein for balloon catheter inflation, said housing having a fluid discharge end and a fluid pressurization end;
    a piston in said housing initially adjacent said fluid pressurization end and movable toward said fluid discharge end;
    means for advancing the piston, said piston advancement means having a longitudinal advancement axis and being engaged with said piston and extending externally of the fluid pressurization end of said housing;
    means for controlling movement of the piston, said piston movement control means being for transversely releasably engaging said piston advancement means, said piston movement control means being in said housing; and
    lever means for engaging said piston movement control means and for moving same out of engagement with said piston advancement means, said lever means being secured to the syringe assembly.

2. The inflation syringe assembly according to claim 1, wherein respective engaging surfaces of said piston advancement means and of said piston movement control means include mating threads, the direction of movement of said piston movement control means being at 90 degrees to the longitudinal advancement axis of said piston advancement means.

3. The inflation syringe assembly according to claim 2, wherein said lever means includes a stop surface and fulcrum means for transversely engaging said stop surface with said piston movement control means.

4. The inflation syringe assembly according to claim 1, wherein said lever means includes a stop surface and fulcrum means for engaging said stop surface with said piston movement control means and for moving said piston control means in a direction that is generally transverse with respect to said longitudinal advancement axis of said piston advancement means.

5. The inflation syringe assembly according to claim 1, wherein the engaging surfaces of said piston advancement means and said piston movement control means include mating threads extending over approximately one half of the circumference of said piston advancement means.

6. The inflation syringe assembly according to claim 1, wherein said piston movement control means includes an internal surface that has an annular shape which is generally oval in cross-section and that has a threaded surface and a generally opposing unthreaded substantially smooth surface.

7. The inflation syringe assembly according to claim 1, wherein said piston advancement means is in the form of a threaded rod that is slidingly received through the fluid pressurization end of said housing, said fluid pressurization end including a support housing through which said rod moves, said piston movement control means including a half nut in said lever housing and receiving said rod therethrough, an internal surface portion of said half nut being threaded, and biasing means urging said threaded surface portion into mating threaded engagement with said rod.

8. The inflation syringe assembly according to claim 7, wherein said lever means includes fulcrum means mounted on said support housing, and stop means aligned with said half nut through said support housing which upon depression of said lever means moves said half nut against said biasing means to disengage said mating threaded engagement of the rod and the half nut.

9. The inflation syringe assembly according to claim 8, wherein said half nut is movable away from said rod in a direction which is 90 degrees to the axis of movement of said rod.

10. The inflation syringe assembly according to claim 9, wherein said mating threaded engagement extends for about one half the circumference of said rod.

11. A syringe assembly for accurate pressurization and rapid depressurization of a balloon catheter, the syringe assembly comprising:
    a first threaded surface for advancement and retraction of a plunger within a barrel of the syringe assembly, said first threaded surface being on an elongated rod in operative interengagement with the barrel;
    a second threaded surface for engagement and disengagement with said first threaded surface to control speed of advancement and retraction of said plunger, said second threaded surface being on a component that is moveable in a direction generally transverse to the first threaded surface;
    means for urging said second threaded surface into engagement with said first threaded surface, said urging means being in the syringe assembly; and
    lever means for overcoming said urging means to hold said second threaded surface out of engagement with said first threaded surface, said lever means being secured to the syringe assembly.

12. The syringe assembly according to claim 11, wherein the direction of movement of said second threaded surface relative to said first threaded surface is 90 degrees.

13. The syringe assembly according to claim 12, wherein said first threaded surface is circumferentially continuous and said second threaded surface is arcuate, the area of engagement between said surfaces being about one half of the circumference of said first threaded surface.

14. The syringe assembly according to claim 11, wherein said first threaded surface is circumferentially continuous and said second threaded surface is arcuate, the area of engagement between said surfaces being about one half of the circumference of said first threaded surface.

15. The syringe assembly according to claim 11, wherein said second threaded surface is defined by a half nut through which said elongated rod extends, and said urging means includes a spring acting on said half nut to maintain said threaded engagement.

16. The syringe assembly according to claim 15, wherein the direction of movement of said second threaded surface is 90 degrees relative to said first threaded surface.

17. The syringe assembly according to claim 15, wherein the area of engagement between said threaded surfaces is about one half the circumference of said rod.

18. The syringe assembly according to claim 17, wherein the direction of movement of said second threaded surface is 90 degrees relative to said first threaded surface.

* * * * *

UNITED STATES PATENT AND TRADEMARK OFFICE
CERTIFICATE OF CORRECTION

PATENT NO. : 4,832,692

DATED : May 23, 1989

INVENTOR(S) : John W. Box and John H. Folger, Jr.

It is certified that error appears in the above-identified patent and that said Letters Patent is hereby corrected as shown below:

Col. 1, line 21, "involve,," should read --involved,--; line 45, "uuch" should read --such--.
Col. 3, line 49, "are" should read --area--; line 57, "th" should read --the--.
Col. 6, line 54, "t force" should read --to force--.

Signed and Sealed this

Twenty-third Day of April, 1991

Attest:

HARRY F. MANBECK, JR.

*Attesting Officer*     *Commissioner of Patents and Trademarks*